United States Patent [19]
Fattore et al.

[11] 4,337,366
[45] Jun. 29, 1982

[54] METHOD FOR THE PREPARATION OF ETHERS

[75] Inventors: Vittorio Fattore; Giovanni Manara; Bruno Notari, all of San Donato Milanese, Italy

[73] Assignee: Snamprogetti S.p.A., Milan, Italy

[21] Appl. No.: 129,163

[22] Filed: Mar. 10, 1980

Related U.S. Application Data

[63] Continuation of Ser. No. 879,769, Feb. 21, 1978, abandoned, which is a continuation of Ser. No. 633,859, Nov. 20, 1975, abandoned.

[30] Foreign Application Priority Data

Nov. 21, 1974 [IT]  Italy .............................. 29683 A/74

[51] Int. Cl.³ ............................................ C07C 41/09
[52] U.S. Cl. ................................ 568/698; 252/453 R
[58] Field of Search ........................................ 568/698

[56] References Cited

U.S. PATENT DOCUMENTS 2,045,560  6/1936  Fenske .
2,282,469  5/1942  Frolich .
2,922,822  1/1960  Beach .
3,033,778  5/1962  Frilette et al. .
3,140,252  7/1964  Frilette et al. .
3,175,967  3/1965  Miale et al. .
3,267,156  8/1966  Hansen .
4,013,589  3/1977  Buonomo et al. .
4,013,590  3/1977  Buonomo et al. .

OTHER PUBLICATIONS

Prevost, Soc. Chim. de France, Bull., 5th series, 1941, pp. 89–100.

*Primary Examiner*—Howard T. Mars
*Attorney, Agent, or Firm*—Morgan, Finnegan, Pine, Foley & Lee

[57] ABSTRACT

In the process for dehydrating an aliphatic alcohol to convert same into the corresponding ether, the improvement consisting in that the catalyst is an active alumina on the surface of which a layer of a silicon compound has been deposited. Long life of the catalyst and improved conversion rates are the main advantages.

16 Claims, 1 Drawing Figure

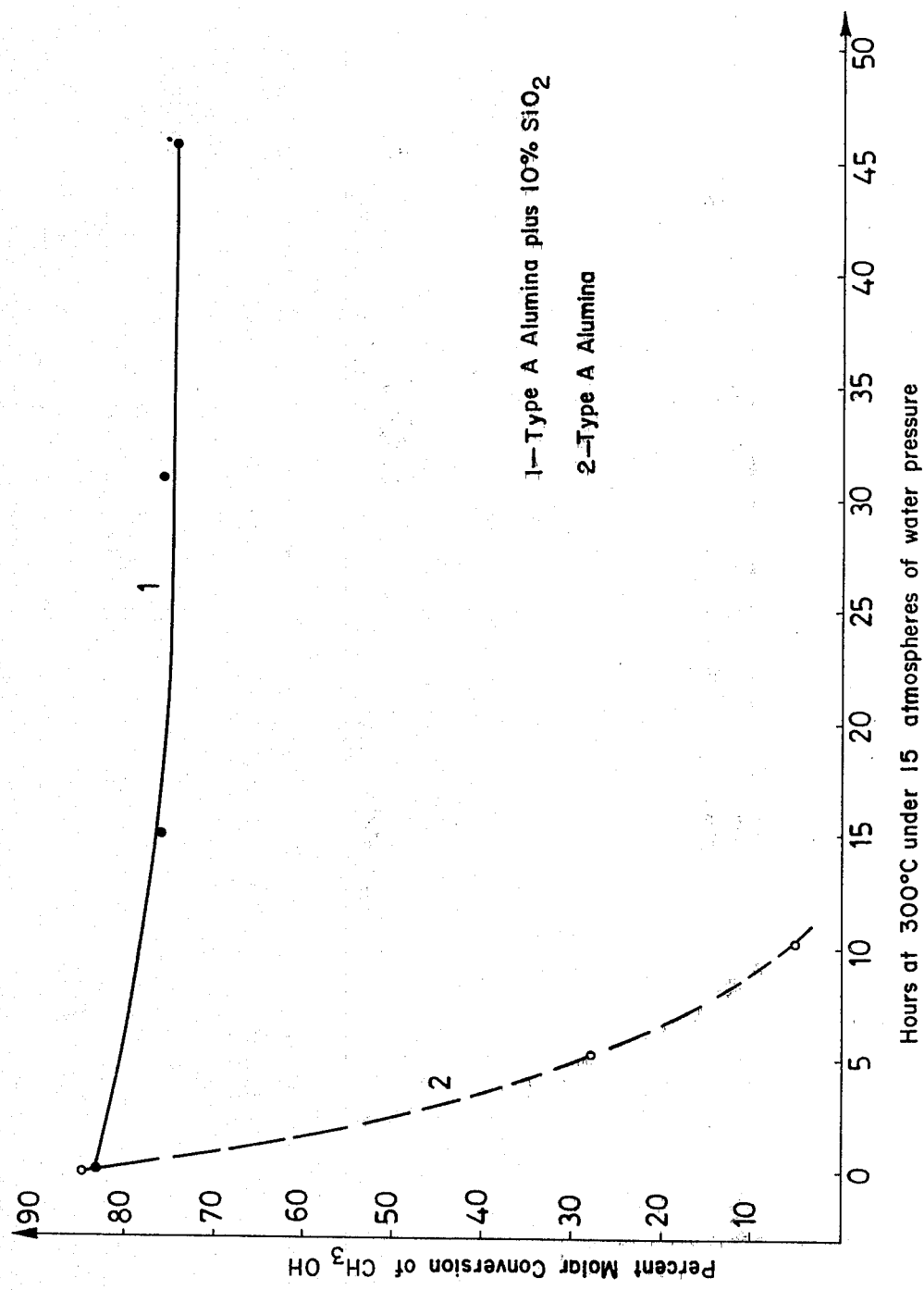

METHOD FOR THE PREPARATION OF ETHERS

This is a continuation of application Ser. No. 879,769, filed Feb. 21, 1978, which in turn is a continuation of application Ser. No. 633,859, filed Nov. 20, 1975, both now abandoned.

This invention relates to a method for the preparation of ethers using alcohols as the starting materials. More particularly, the subject-matter of this invention is a method of dehydration of aliphatic alcohols, which is carried out at a high temperature in the presence of a catalyst, the latter being essentially constituted by active alumina which has been superficially modified by deposition of silica thereon.

The dehydration of alcohols to ethers is known, but, heretofore, the conventional methods did not prove to be particularly satisfactory due to the low selectivity and the rapid decay of the used catalysts.

It has now been found that it is possible positively to improve the results of the dehydration of alcohols to ethers by causing the reaction to take place in the presence of active alumina which has previously been treated with silicon compounds so as to deposit on the alumina surface a layer of oxygen compounds of silicon.

It is thus the subject matter of the present invention a method for the dehydration of aliphatic alcohols to ethers, the method consisting in contacting the alcohol with a catalyst, the latter being obtained by reacting an active alumina, preferably a gamma and eta alumina, with a silicon compound, according to what has been disclosed in the French Patent Applications Nos. 74.35462 and 74.35463 dated Oct. 22, 1974 (corresponding to German DOS Nos. P2451850 and P2451849 of Oct. 31, 1974 respectively) of the same Applicants.

According to the above mentioned applications, it is possible to improve the mechanical properties of materials formed by metallic oxides by treating such materials with a silicon compound and subjecting the thusly obtained product to drying and to a controlled oxidation.

Silicon compounds which can be used have the general formula:

wherein X, Y, Z and W can be —R, —OR, —Cl, —Br, —SiH$_3$, —COOR, SiH$_n$Cl$_m$, R being hydrogen, aryl, an alkyl, cycloalkyl-aromatic, alkyl-aromatic and alkyl-cycloalkyl radical having from 1 to 30 carbon atoms, such as methyl, ethyl, isopropyl, n-propyl, n-butyl, iso-butyl, cyclohexyl, cyclopentyl, phenyl, phenylcyclohexyl, alkylphenyl, n and m being integers comprised between 1 and 3.

Among the above listed compounds the esters of the orthosilicic acid are preferred such as the tetrasilicates of methyl, ethyl, propyl, isopropyl, isobutyl and n-butyl.

The materials which can be treated according to the above outlined method are all the oxides, more particularly the oxides of aluminum, the oxides of titanium, the oxides of magnesium, silica, chromium oxides, zirconium oxides, iron oxides and the admixtures of these oxides as such or also with other compounds.

It has now been found that, in particular case of the aluminas, the above suggested method renders them stabler in time in the dehydration of alcohols. The catalyst thus obtained, in fact, is highly resistant to the hydrothermal conditions which are experienced during the dehydration reaction, in that the superficial layer of silica, which is formed due to the reaction between the superficial —OH groups of alumina and the ester of the silicic acid improves the resistance of alumina (gamma and eta) to sintering. This fact is conductive to a longer life of such catalysts as compared with the conventional ones and, summing up, to an improved plant economy.

The cracking and decomposition side reactions are unimportant and the catalyst decay is positively slower than that of the catalysts as suggested heretofore for dehydration reactions.

The catalyst is so prepared as to deposit on the surface of alumina from 0.5% to 20% by weight of silica, and preferably from 3% to 12%, as calculated on the final overall weight of the catalyst. Several preparation procedures can be employed as disclosed in the prior Patent Applications as indicated above in the name of the same Applicants.

The dehydration process according to the present invention is carried out by contacting the alcohol concerned, also in the presence of alkanes or other inert gases such as nitrogen or CO$_2$, with the catalyst, at a temperature in the range from 200° C. to 400° C. and preferably between 250° C. and 350° C. in either a fixed or a fluid bed. The reaction pressure can be selected among those which are most appropriate for the particular alcohol being treated but generally comprised between atmospherical pressures and 200 atmospheres. The spatial feeding velocity, as expressed in terms of W.H.S.V. can be varied between 0.1 and 20, and preferably between 0.2 and 10.

Among the alcohols which can be considered for the present process, methyl, ethyl and isopropyl-alcohol can be indicated.

The dehydration process can be carried out either alone or concurrently with other reactions, such as the synthesis of the alcohol, such as methanol.

EXAMPLE 1

This Example relates to the preparation of the catalyst according to what has been disclosed in the Patent Application No. 74.35462 (DOS P24 51 850).

100 grams of alumina are introduced in an autoclave (self-heating type) together with 40 grams of (C$_2$H$_5$O$_4$)$_4$Si. The autoclave is evacuated and scavenged with nitrogen a few times to remove any traces of oxygen, whereafter it is charged with nitrogen under a pressure of 5 kilograms/sq. centimeter. The autoclave is heated to 200° C. and maintained at this temperature during 4 hours. On completion, the autoclave is cooled, the pressure is released and alumina is recovered to be subjected to a subsequent heat treatment during 2 hours at 200° C. in nitrogen and then to a calcination in air at 500° C. during 4 hours. The alumina thus treated is analyzed and gives a silica contents of about 10%. The thusly obtained sample is used in the methanol dehydration reaction, as will be disclosed in more detail in the following Examples.

EXAMPLE 2

A commercial gamma-alumina of the A type in spherules of about 3-4 millimeters in diameter, the properties of which are reported in TABLE 1, is activated at 450° C. under a nitrogen stream.

By comparison a fraction of such alumina is used as such, while a second portion is treated with tetraethylorthosilicate according to the procedure and the dosages as reported in EXAMPLE 1, so that the contents of silica on the thusly treated alumina is 10.2%.

TABLE 1

| Properties of the "A" alumina | |
| --- | --- |
| Poured specific gravity | 0.51 grams/cu.cm. |
| Superficial area | 301 sq.meters/gram |
| Overall pore volume | 0.83 cu.cm/gram |

A fixed bed tubular reactor is charged one time with 1 gram of alumina as treated with silicon derivatives and the subsequent time with 1 g of untreated alumina, is heated to 300° C. under a nitrogen stream of 400 mls an hour under atmospherical pressure and subsequently fed with methanol at a spatial velocity of 1 gram/gram an hour.

The effluents of the reactor, as formed by nitrogen, dimethyl ether, unconverted methanol and water, is gaschromatografically analyzed without detecting any by-products.

The analysis gives the results as tabulated in TABLE 2.

TABLE 2

| Dehydration of methanol to dimethyl ether | | |
| --- | --- | --- |
| Catalyst | Alumina Type A | Alumina A plus 10.2% SiO$_2$ |
| Temperature, °C. | 300 | 300 |
| Pressure, atmospheres | 1 | 1 |
| Spat.veloc.g/g per hour | 1 | 1 |
| CH$_3$OH conversion, molar % | 84 | 83 |

From the data of TABLE 2 it can clearly be seen that, within the limits of the experimental errors, the treatment with tetraethyl orthosilicate did not vary the catalytic properties of the A alumina in the methanol dehydration reaction.

Inasmuch as it is known that in this field of temperature the water vapour gradually reduces in time the activity of the alumina and that in the dehydration of an alcohol to an ether a partial water pressure is always present, a quick aging of both catalysts has been attempted by exposing them to a certain steam pressure. The alumina "A" and the same alumina with 10.2% of silica have been subjected to a treatment at 300° C. under a pressure of 15 atmospheres of water, using the same apparatus as described above.

From time to time, water was vented and the catalyst dried during 10 hours still at 300° C. and under atmospherical pressure under a nitrogen stream of 400 mls an hour. Methanol is then fed under the same conditions as described above and the results of the analyses of the effluents from the reactor with catalysts subjected to the treatment with water during progressive times are tabulated in TABLE 3.

TABLE 3

| Dehydration of methanol to dimethyl ether | | |
| --- | --- | --- |
| Catalyst | "A" alumina | "A" alumina plus 10.2% SiO$_2$ |
| Temperature, °C. | 300 | 300 |
| Pressure, atmospheres | 1 | 1 |
| Spatial veloc.g/g. hour | 1 | 1 |

TABLE 3-continued

| Dehydration of methanol to dimethyl ether | | | | | |
| --- | --- | --- | --- | --- | --- |
| Catalyst | "A" alumina | "A" alumina plus 10.2% SiO$_2$ | | | |
| Hours of treatm. at 300° C. with 15 atmosph. water | - | 5 | 10 | 15 | 31 | 46 |
| Conversion of CH$_3$OH, molar % | 28 | 5 | 77 | 77 | 75 |

To render the data of TABLE 2 and TABLE 3 better comparable the figure of the drawings reports the variation of the conversion of methanol (ordinates) as a function of the hours of treatment to 300° C. under 15 atmospheres of water pressure (plot 1=Al$_2$O$_3$ (A) plus 10.2% SiO$_2$; plot 2=Al$_2$O$_3$ (A). The A alumina after 5 hours only reduces its catalytic activity in a drastic manner, with a 28% conversion over the initial 84% and, after 10 hours the activity drops to 5%.

The drop of the dehydrating activity is accompanied by the sintering of alumina the superficial area of which falls in 10 hours to 108 sq. meters per gram.

Conversely, the A alumina containing 10.2% of silica, after the treatment at 300° C. under a pressure of 15 atmospheres of water, varies its catalytic activity only slightly so that after 46 hours, the conversion of methanol is stable at about 75%. Also the superficial area of the catalyst decays at a much slower rate; after 46 hours it is still at 232 sq. meters per gram.

The silicization process has thus permitted to maintain the dehydrating properties of alumina unaltered even after a long handling at 300° C. in an atmosphere of water, under such conditions as the alumina which had not been treated with silicon derivatives rapidly decayed.

This result makes it clearly conspicuous that the silicized alumina, as it maintains its properties unaltered with the lapse of time, can profitably be employed in an improved industrial process for dehydrating methanol.

EXAMPLE 3

"A" alumina and "A" alumina containing 10.2% silica, as already described in EXAMPLE 2, have been subjected to aging in the presence of water vapour by operating under conditions which were less drastic than the previous ones.

Two samples of the two aluminas have been allowed to age during 512 hours at 300° C. under a pressure of 5.5 atmospheres of steam and 2 atmospheres of nitrogen.

Samples have been periodically drawn of the two aluminas to follow with the lapse of time with the methanol dehydrating test, the variations of the catalytic activity.

The conversion percentages of the two aluminas which had not been subjected to aging are reported in TABLE 2.

TABLE 4 reports the catalytic activity as a function of the time of aging.

TABLE 4

| Aging of catalysts at 300° C. and 5.5 atmospheres of steam | | |
| --- | --- | --- |
| Catalyst | "A" alumina | "A" alumina with 10.2% TDS |
| Reaction temper. °C. | 300 | 300 |
| Reaction press. atmosph. | 1 | 1 |
| Spatial vel.methanol g/g.h | 1 | 1 |
| Hours of treatment at 300° C. | | |

TABLE 4-continued

Aging of catalysts at 300° C. and 5.5 atmospheres of steam

| Catalyst | "A" alumina | "A" alumina with 10.2% TDS |
|---|---|---|
| under 5.5 atmosph. H₂O and 2 atmosph. nitrogen | 36 115 210 512 | 36 115 210 512 |
| Conversion CH₃OH, molar % | 79 79 72 61 | 79 78 78 78 |

It is thus apparent that the decay is much slower than that described in Example 2 where 15 atmospheres of steam were the working pressure; after 210 hours the loss of activity is rather low for "A" alumina. By prolonged treatment up to 512 hours, however, it is seen that "A" alumina decays in a positive manner, whereas the same alumina but containing 10.2% of $SiO_2$ maintains its activity unaffected.

EXAMPLE 4

A commercial "B" gamma alumina having the properties tabulated in TABLE 5 is partly used as such, for comparison purpose, and partly treated with 40 grams of tetraethyl orthosilicate according to the procedure described in EXAMPLE 1, so that the silica contents in the catalyst is 8.1%.

TABLE 5

Properties of "B" alumina

| Poured specific gravity | 0.95 grams/cu.cm. |
|---|---|
| Superficial area | 210 sq.meters/gram |
| Overall pore volume | 0.40 cu.cm/gram |

Both the untreated and the treated alumina are subjected to aging in the presence of water vapour, by operating under the same conditions as in EXAMPLE 2, that is, at 280° C. under a pressure of 15 atmospheres of steam.

Water is periodically discharged and the catalyst is dried, still at 280° C. under a nitrogen stream, whereafter methanol is fed in.

TABLE 6 reports the catalytic activities of the two aluminas in the dehydration of methanol to dimethyl ether as a function of the aging time.

TABLE 6

Dehydration of methanol to dimethyl ether

| Catalyst | "B" alumina | "B" alumina with 8.1% SiO₂ |
|---|---|---|
| Temperature,°C. | 280 | 280 |
| Pressure,atmosph. | 1 | 1 |
| Spat.vel.g/g.h | 0.8 | 0.8 |
| Hours of treatment at 300° C. under 15 atmosph. of H₂O | 0 5 10 168 | 0 5 10 36 52 168 |
| CH₃OH convers.molar % | 76 10 4 2 | 75 74 73 73 72 71 |

The superficial area of the "B" alumina after 168 hours at 280° C. under 30 atmospheres of water falls to 90 sq. meters/gram whereas that of the same alumina containing 8.1% silica under the same conditions drops from the initial 210 sq. meters/gram to 195 sq. meters/gram.

The silicization process has permitted to maintain virtually unaltered the dehydrating properties of the "B" alumina even after a long lasting treatment at 280° C. in an atmosphere of steam, under conditions in which the same alumina which had not been treated with silicon derivatives rapidly decays.

What we claim is:

1. A method for the preparation of aliphatic ethers comprising dehydrating an aliphatic alcohol at a temperature between 200° and 400° C. in the presence of a catalyst produced by the steps of:

(a) reacting active alumina with a silicon compound of general formula

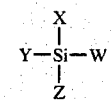

wherein X, Y, Z, and W are each selected from the group consisting of —R, —OR, —Cl, —Br, —SiH₃, —COOR and —SiH$_n$Cl$_m$, R is a hydrogen atom of an alkyl, cycloalkyl, aryl, alkyl-aromatic or alkyl-cycloalkyl radical having from 1 to 30 carbon atoms and m and n are integers of from 1 to 3;

(b) drying the product of step (a); and (c) calcining in air the dried product of step (b) thereby depositing on said alumina from 0.5% to 20% by weight, calculated on the final overall weight of said catalyst, of silica formed by the above reaction.

2. A method for the preparation of aliphatic ethers comprising dehydrating an aliphatic alcohol having from 1 to 6 carbon atoms at a temperature between 200° and 400° C. in the presence of a catalyst produced by the steps of:

(a) reacting active alumina with a silicon compound of general formula

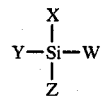

wherein X, Y, Z, and W are each selected from the group consisting of —R, —OR, —Cl, —Br, —SiH₃, —COOR and —SiH$_n$Cl$_m$, R is a hydrogen atom or an alkyl, cycloalkyl, aryl, alkyl-aromatic or alkyl-cycloalkyl radical having from 1 to 30 carbon atoms and m and n are integers of from 1 to 3;

(b) drying the product of step (a); and (c) calcining in air the dried product of step (b) thereby depositing on said alumina from 0.5% to 20% by weight, calculated on the final overall weight of said catalyst, of silica formed by the above reaction.

3. A method for the preparation of aliphatic ethers comprising reacting an alcohol selected from methanol, ethanol, isopropanol at a temperature between 200° and 400° C. in the presence of a catalyst produced by the steps of:

(a) reacting active alumina with a silicon compound of general formula

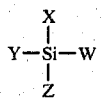

wherein X, Y, Z, and W are each selected from the group consisting of —R, —OR, —Cl, —Br, —SiH$_3$, —COOR and —SiH$_n$Cl$_m$, R is a hydrogen atom or an alkyl, cycloalkyl, aryl, alkyl-aromatic or alkyl-cycloalkyl radical having from 1 to 30 carbon atoms and m and n are integers of from 1 to 3;

(b) drying the product of step (a); and (c) calcining in air the dried product of step (b) thereby depositing on said alumina from 0.5% to 20% by weight, calculated on the final overall weight of said catalyst, of silica formed by the above reaction.

4. The method of claim 3 wherein the silica comprises from 3 to 12 percent by weight of the total catalyst.

5. The method of claim 3 wherein the aliphatic alcohol is reacted at a temperature of from 250° to 350° C.

6. The method of claim 3 wherein the aliphatic alcohol is reacted at a pressure of from 1 to 200 atmospheres.

7. The method of claim 3 wherein the aliphatic alcohol is reacted at a spatial velocity of from 0.1 to 20 W.H.S.V.

8. The method of claim 7 wherein the aliphatic alcohol is reacted at a spatial velocity of from 0.2 to 10 W.H.S.V.

9. The method of claim 3 wherein the product of step (c) is calcined at 500° C.

10. A method for the preparation of aliphatic ethers comprising dehydrating aliphatic alcohols selected from methanol, ethanol and isopropanol, at a temperature between 200° and 400° C. in the presence of a catalyst comprised of active alumina having a layer of silica deposited thereon, the silica comprising from 0.5 to 20 percent by weight of the total catalyst.

11. The method of claim 10 wherein the silica comprises from 3 to 12 percent by weight of the total catalyst.

12. The method of claim 10 wherein the aliphatic alcohol is reacted at a temperature of from 250° to 350° C.

13. The method of claim 10 wherein the aliphatic alcohol is reacted at a pressure of from 1 to 200 atmospheres.

14. The method of claim 10 wherein the aliphatic alcohol is reacted at a spatial velocity of from 0.1 to 20 W.H.S.V.

15. The method of claim 10 wherein the aliphatic alcohol is reacted at a spatial velocity of from 0.2 to 10 W.H.S.V.

16. A method for the preparation of aliphatic ethers comprising dehydrating aliphatic alcohols selected from methanol, ethanol and isopropanol, at a temperature between 200° and 400° C. in the presence of a catalyst comprised of active alumina having a layer of silica deposited thereon, said layer comprising from 0.5 to 20 percent by weight of the total catalyst and said catalyst being produced by the steps of:

(a) reacting active alumina with a compound selected from the tetrasilicates of methyl, ethyl, propyl, isopropyl, isobutyl and n-butyl;

(b) drying the product of step (a); and (c) calcining in air the dried product of step (b).

* * * * *